United States Patent
Yang et al.

(10) Patent No.: US 9,990,470 B2
(45) Date of Patent: Jun. 5, 2018

(54) CARDIAC MAPPING SYSTEM AND METHOD FOR VOLTAGE-BASED EVALUATION OF ELECTROGRAMS

(71) Applicant: St. Jude Medical, Cardiology Division, Inc., St. Paul, MN (US)

(72) Inventors: Chin-Ann Yang, Minneapolis, MN (US); Valtino X. Afonso, Oakdale, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 704 days.

(21) Appl. No.: 14/527,015

(22) Filed: Oct. 29, 2014

(65) Prior Publication Data

US 2015/0120207 A1    Apr. 30, 2015

Related U.S. Application Data

(60) Provisional application No. 61/897,597, filed on Oct. 30, 2013.

(51) Int. Cl.
*A61B 5/04* (2006.01)
*G06F 19/00* (2018.01)
(Continued)

(52) U.S. Cl.
CPC ...... *G06F 19/3431* (2013.01); *A61B 5/04012* (2013.01); *A61B 5/046* (2013.01); *A61B 5/0422* (2013.01)

(58) Field of Classification Search
CPC ... A61B 5/04012; A61B 5/0422; A61B 5/046; A61B 5/0452; A61B 2576/023; G06F 19/3431
See application file for complete search history.

(56) References Cited

U.S. PATENT DOCUMENTS

| | | | |
|---|---|---|---|
| 4,453,551 A | 6/1984 | Anderson et al. | |
| 5,056,527 A | 10/1991 | Go et al. | |

(Continued)

FOREIGN PATENT DOCUMENTS

| | | |
|---|---|---|
| CA | 2813586 A1 | 10/2013 |
| CN | 103038772 A | 4/2013 |

(Continued)

OTHER PUBLICATIONS

International Search Report and Written Opinion in PCT Application No. PCT/US2014/062778 (dated Jan. 21, 2015).

(Continued)

*Primary Examiner* — Mallika D Fairchild
(74) *Attorney, Agent, or Firm* — Armstrong Teasdale LLP

(57) ABSTRACT

Systems and methods for evaluating electrograms are described. An example method of evaluating an electrogram such as an atrial and/or ventricular electrogram containing a plurality of data samples each having a voltage includes selecting an activity interval for the electrogram, calculating an energy level for each window of a plurality of windows of the electrogram based on the voltages of the data samples in each window, assigning the calculated energy levels to a plurality of bins, and calculating an index based at least in part on a number of energy levels assigned to a particular bin of the plurality of bins.

32 Claims, 9 Drawing Sheets

(51) Int. Cl.
*A61B 5/046* (2006.01)
*A61B 5/042* (2006.01)

(56) References Cited

U.S. PATENT DOCUMENTS

| | | |
|---|---|---|
| 6,434,417 B1 | 8/2002 | Lovett |
| 8,229,545 B2 | 7/2012 | Afonso |
| 8,359,092 B2 | 1/2013 | Hayam et al. |
| 8,647,284 B2 | 2/2014 | Afonso |
| 8,676,305 B2 | 3/2014 | Hayam et al. |
| 8,862,213 B2 | 10/2014 | Lo et al. |
| 2005/0256414 A1* | 11/2005 | Kettunen ............... A61B 5/024 600/509 |
| 2010/0317981 A1 | 12/2010 | Grunwald |
| 2012/0089038 A1 | 4/2012 | Ryu et al. |
| 2013/0211274 A1* | 8/2013 | Lai ....................... A61B 5/7221 600/529 |
| 2013/0253349 A1 | 9/2013 | Hayam et al. |

FOREIGN PATENT DOCUMENTS

| | | |
|---|---|---|
| EP | 0554605 | 8/1993 |
| JP | H03-066358 | 3/1991 |
| WO | 2013/123549 | 8/2013 |
| WO | 2014058664 A1 | 4/2014 |

OTHER PUBLICATIONS

Takahashi et al., "Characterization of Electrograms Associated With Termination of Chronic Atrial Fibrillation by Catheter Ablation," J Am Coll Cardiol, vol. 51, No. 10, pp. 1003-1010, Mar. 11, 2008.

Gan Esan et al., "Bipolar Electrogram Shannon Entropy at Sites of Rotational Activation Implications for Ablation of Atrial Fibrillation," Circ Arrhythm Electrophysiol, vol. 6, No. 1, pp. 48-57, 2013. Epub Dec. 23, 2012.

Verma et al., "Selective CFAE Targeting for Atrial Fibrillation Study (SELECT AF): A Multicenter, Randomized Trial," Circ Arrhythm Electrophysiol, vol. 7, p. 55-62, Epub Jan. 14, 2014.

* cited by examiner

CARDIAC MAPPING SYSTEM AND METHOD FOR VOLTAGE-BASED EVALUATION OF ELECTROGRAMS

CROSS-REFERENCE TO RELATED APPLICATIONS

This application claims priority to provisional application Ser. No. 61/897,597, filed Oct. 30, 2013, the entire specification of which is incorporated herein.

BACKGROUND OF THE DISCLOSURE

A. Field of the Disclosure

The present disclosure relates generally to an electrophysiology system and method used to measure electrical activity occurring in the heart of a patient and to visualize the electrical activity and/or information related to the electrical activity. More particularly, the present disclosure relates to processing of data to detect and evaluate complex fractionated electrograms and the use of such data in three-dimensional mapping of the electrical activity associated with complex fractionated electrograms.

B. Background Art

The heart contains two specialized types of cardiac muscle cells. The majority, around ninety-nine percent, of the cardiac muscle cells is contractile cells, which are responsible for the mechanical work of pumping the heart. Autorhythmic cells comprise the second type of cardiac muscle cells, which function as part of the autonomic nervous system to initiate and conduct action potentials responsible for the contraction of the contractile cells. The cardiac muscle displays a pacemaker activity, in which membranes of cardiac muscle cells slowly depolarize between action potentials until a threshold is reached, at which time the membranes fire or produce an action potential. This contrasts with a nerve or skeletal muscle cell, which displays a membrane that remains at a constant resting potential unless stimulated. The action potentials, generated by the autorhythmic cardiac muscle cells, spread throughout the heart triggering rhythmic beating without any nervous stimulation.

The specialized autorhythmic cells of cardiac muscle comprising the conduction system serve two main functions. First, they generate periodic impulses that cause rhythmical contraction of the heart muscle. Second, they conduct the periodic impulses rapidly throughout the heart. When this system works properly, the atria contract about one sixth of a second ahead of ventricular contraction. This allows extra filling of the ventricles before they pump the blood through the lungs and vasculature. The system also allows all portions of the ventricles to contract almost simultaneously. This is essential for effective pressure generation in the ventricular chambers. The rates at which these autorhythmic cells generate action potentials differ due to differences in their rates of slow depolarization to threshold in order to assure the rhythmical beating of the heart.

Normal autorhythmic cardiac function may be altered by neural activation. The medulla, located in the brainstem above the spinal cord, receives sensory input from different systemic and central receptors (e.g., baroreceptors and chemoreceptors) as well as signals from other brain regions (e.g., the hypothalamus). Autonomic outflow from the brainstem is divided principally into sympathetic and parasympathetic (vagal) branches. Efferent fibers of these autonomic nerves travel to the heart and blood vessels where they modulate the activity of these target organs. The heart is innervated by sympathetic and vagal fibers. Sympathetic efferent nerves are present throughout the atria (especially in the sinoatrial node) and ventricles, including the conduction system of the heart. The right vagus nerve primarily innervates the sinoatrial node, whereas the left vagus nerve innervates the atrial-ventricular node; however, there can be significant overlap in the anatomical distribution. Efferent vagal nerves also innervate atrial muscle. However, efferent vagal nerves only sparsely innervate the ventricular myocardium. Sympathetic stimulation increases heart rate and conduction velocity, whereas parasympathetic (vagal) stimulation of the heart has opposite effects.

An arrhythmia occurs when the cardiac rhythm becomes irregular, i.e., too fast (tachycardia) or too slow (bradycardia), or the frequency of the atrial and ventricular beats are different. Arrhythmias can develop from either altered impulse formation or altered impulse conduction. The former concerns changes in rhythm that are caused by changes in the pacemaker cells resulting in irregularity or by abnormal generation of action potentials by sites other than the sinoatrial node, i.e., ectopic foci. Altered impulse conduction is usually associated with complete or partial blockage of electrical conduction within the heart. Altered impulse conduction commonly results in reentry, which can lead to tachyarrhythmias. Reentry can take place within a small local region or it can occur, for example, between the atria and ventricles (global reentry). Reentry requires the presence of a unidirectional block within a conducting pathway usually caused by partial depolarization of the pacemaker cells. Arrhythmias can be either benign or more serious in nature depending on the hemodynamic consequences of arrhythmias and their potential for changing into lethal arrhythmias.

Electrophysiology studies may be used to identify and treat these arrhythmias. In one exemplary system, a measurement system introduces a modulated electric field into the heart chamber. The blood volume and the moving heart wall surface modify the applied electric field. Electrode sites within the heart chamber passively monitor the modifications to the field and a dynamic representation of the location of the interior wall of the heart is developed for display to the physician. Electrophysiology signals generated by the heart itself are also measured at electrode sites within the heart and these signals are low pass filtered and displayed along with the dynamic wall representation. This composite dynamic electrophysiology map may be displayed and used to diagnose the underlying arrhythmia.

In addition to mapping for diagnosis, the measurement system can also be used to physically locate a therapy catheter in a heart chamber. A modulated electrical field delivered to an electrode on this therapy catheter can be used to show the location of the therapy catheter within the heart. The therapy catheter location can be displayed on the dynamic electrophysiology map in real time along with the other diagnostic information. Thus the therapy catheter location can be displayed along with the intrinsic or provoked electrical activity of the heart to show the relative position of the therapy catheter tip to the electrical activity originating within the heart itself. Consequently, the physician can guide the therapy catheter to any desired location within the heart with reference to the dynamic electrophysiology map.

The dynamic electrophysiology map is generally produced in a step-wise process. First, the interior shape of the heart is determined. This information is derived from a sequence of geometric measurements related to the modulation of the applied electric field. Knowledge of the dynamic shape of the heart is used to generate a representation of the interior or exterior surface of the heart. Next, the intrinsic electrical activity of the heart is measured. The signals of physiologic origin are passively detected and processed such that the magnitude of the potentials on the wall surface may be displayed on the wall surface representation. The measured electrical activity is displayed on the wall surface representation in any of a variety of formats, for example, in various colors or shades of a color. Finally, a location current may be delivered to a therapy catheter within the same chamber. The potential sensed from this current may be processed to determine the relative or absolute location of the therapy catheter within the chamber. These various processes occur sequentially or simultaneously several hundred times a second to give a continuous image of heart activity and the location of the therapy device.

If ablation is the indicated therapy, then a therapy catheter is positioned at the desired location within the heart and energy is delivered to the therapy catheter to ablate the tissue. The use of complex fractionated atrial electrograms (CFAEs) has become one tool used to identify atrial fibrillation ablation sites. For example, in one method, utilized in the EnSite™ Velocity™ mapping system available from St. Jude Medical, a set of activation events are recognized in the CFAE signal, and then time intervals between subsequent activation events are calculated. The average time interval is determined and designated as the CFE mean. Locations whose cycle length is shorter than a predetermined threshold (e.g., 120 milliseconds (ms)) are identified as potential ablation sites.

Other known systems use various other metrics to detect, characterize, and/or evaluate CFAEs. For example, some systems use a CFE standard deviation (CFE StdDev) by detecting activations and computing the standard deviation of the cycle length between successive detected activations. In other systems, the shortest interval between activation detections is used as an index (sometimes referred to as Shortest Complex Interval (SCI)) for the investigation of CFAEs, while other systems use an average of all CFAE complex intervals (ACI) in a signal. An Interval Confidence Level (ICL) is used by some other systems. The ICL is the number of intervals during a recording period that have a length between 70 ms and 120 ms. Some systems utilize a frequency based metric, such as a Dominant Frequency (DF) metric. In systems using the DF metric, the time based electrogram is transformed into frequency space and the most dominant frequency component in the transformed electrogram is identified as the DF.

The various known cycle length based metrics, e.g., CFE mean, CFE StdDev, SCI, ACI, and ICL, used in evaluation of CFAEs depend on accurate activation detection results. Activation detection results are highly dependent on parameter settings. Tuning to the proper parameter settings can be difficult and time consuming. Moreover, if a signal has varying properties, it may be very difficult to find optimal parameters that are applicable to the entire signal. It is thus desirable to provide accurate, useful metric(s) for CFAE analysis that are insensitive to activation detection.

BRIEF SUMMARY OF THE DISCLOSURE

In one embodiment, a computer implemented method for evaluating an electrogram containing a plurality of data samples each having a voltage is described. The computer implemented method includes selecting an activity interval for the electrogram, calculating an energy level for each window of a plurality of windows of the electrogram based on the voltages of the data samples in each window, assigning the calculated energy levels to a plurality of bins, and calculating an index based at least in part on a number of energy levels assigned to a particular bin of the plurality of bins.

In another embodiment, a system for evaluating an electrogram containing a plurality of data samples each having a voltage includes a computing device configured to receive the data samples is described. The computing device includes a processor and at least one memory device coupled to the processor. The memory device stores computer-executable instructions that, when executed by the processor, cause the computing device to: calculate an energy level for each window of a plurality of windows of the electrogram based on the voltages of the data samples in each window, assign the calculated energy levels to a plurality of bins, and calculate an index based at least in part on a number of energy levels assigned to a particular bin of the plurality of bins.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the drawings.

DETAILED DESCRIPTION OF THE DISCLOSURE

The present disclosure relates generally to mapping systems and methods for mapping anatomic structures, such as the human heart or portions thereof, and more particularly to the processing of data from atrial electrograms—such as complex fractionated atrial electrograms (CFAEs) and the use of such data in the mapping system. In particular embodiments, the systems and methods of the present disclosure use a voltage based matrix for evaluation of CFAEs. While in the embodiments herein the systems and methods are used for activation detection in fractionated electrograms, it is contemplated that the systems and methods disclosed herein may be used in non-fractionated electrograms as well. Additionally, while the various embodiments herein are described in connection with mapping of a patient's heart, it is understood that the present disclosure is not limited to mapping of a heart, and that mapping of other anatomic structures is considered to be within the scope of the present disclosure.

Known systems and methods exist for generating a three-dimensional model of an anatomic structure such as the heart, including systems that utilize technology such as CT scanning, MRI, ultrasound imaging, radar imaging, x-ray imaging, and fluoroscopic imaging. The output of such data may be a plurality of x-y-z data coordinates, spherical coordinates and/or other formats to provide a three-dimensional image. Such imaging technology is often useful in diagnosis as well as preparing for a patient's treatment and/or surgery. The imaging process may be performed hours or days before treatment and/or surgery, or concomitantly with the treatment and/or surgery. Some three-dimensional models utilize a segmented approach, including for example a segmented CT or MRI scan image. A segmented model indicates that a subregion of a three-dimensional image has been digitally separated from a larger three-dimensional image, e.g., an image of the right atrium separated from the rest of the heart. Other methodologies and techniques for creating a three-dimensional model of a portion of the patient may also be utilized in accordance with the present disclosure.

Data acquired from the imaging process is typically used to partition the three-dimensional model into discrete surface elements to facilitate numerical computation during subsequent mapping and reconstruction. It is understood that various computational methods may be used to partition the three-dimensional model into discrete segments, such as finite differences, Finite Element Methods (FEM) and Boundary Element Methods (BEM) such as spline BEM or linear BEM. The three-dimensional model of the anatomic structure generally includes a boundary surface defined by the discrete segments, with the boundary surface thus defining an interior (broadly, a first side) of the three-dimensional model and an exterior (broadly, a second side) of the three-dimensional model of the anatomic structure.

Figure 1:
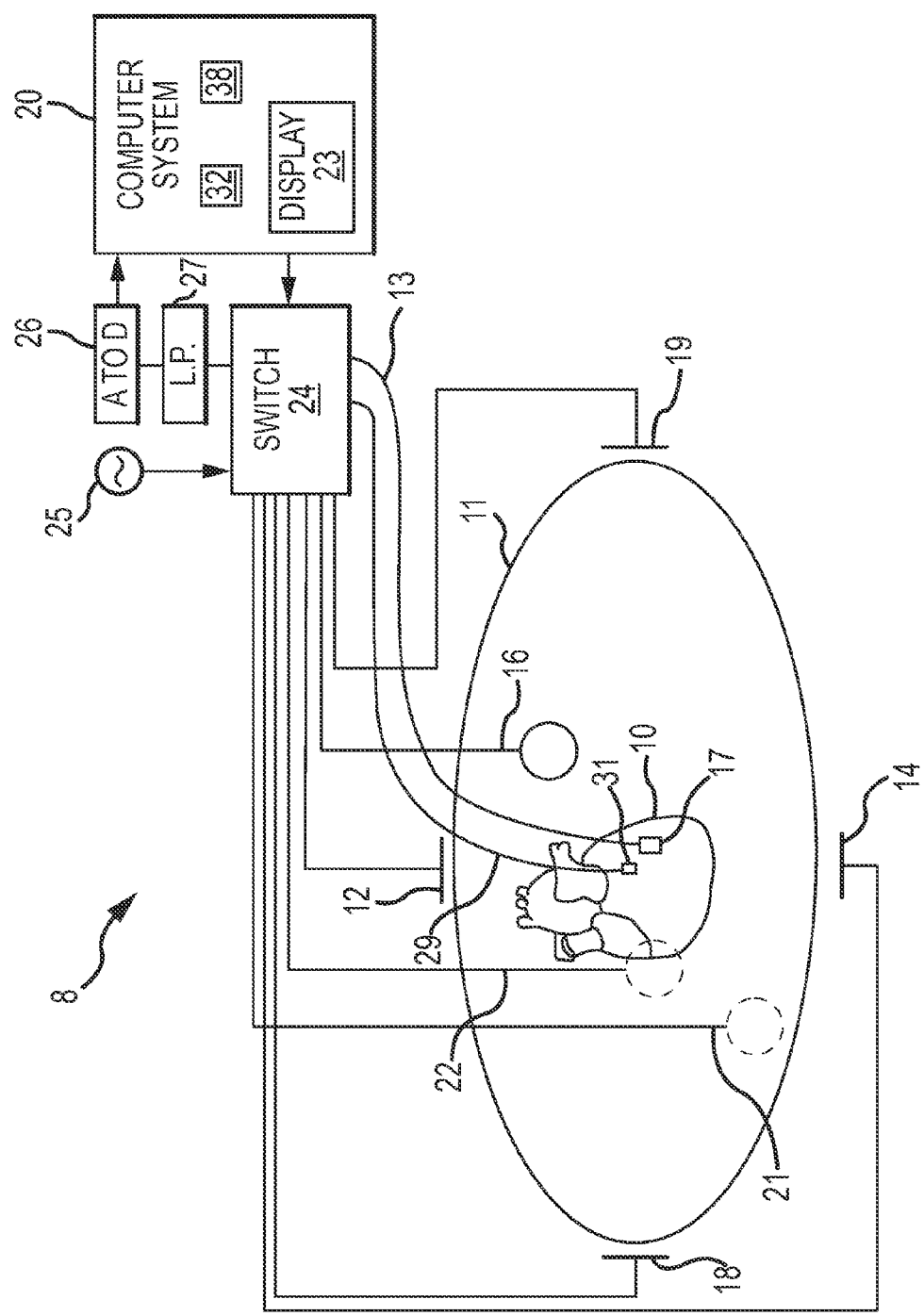
FIG. 1 is a schematic diagram of a system for performing a cardiac electrophysiology examination or ablation procedure wherein the location of one or more electrodes can be determined and recorded.
Figure 2:
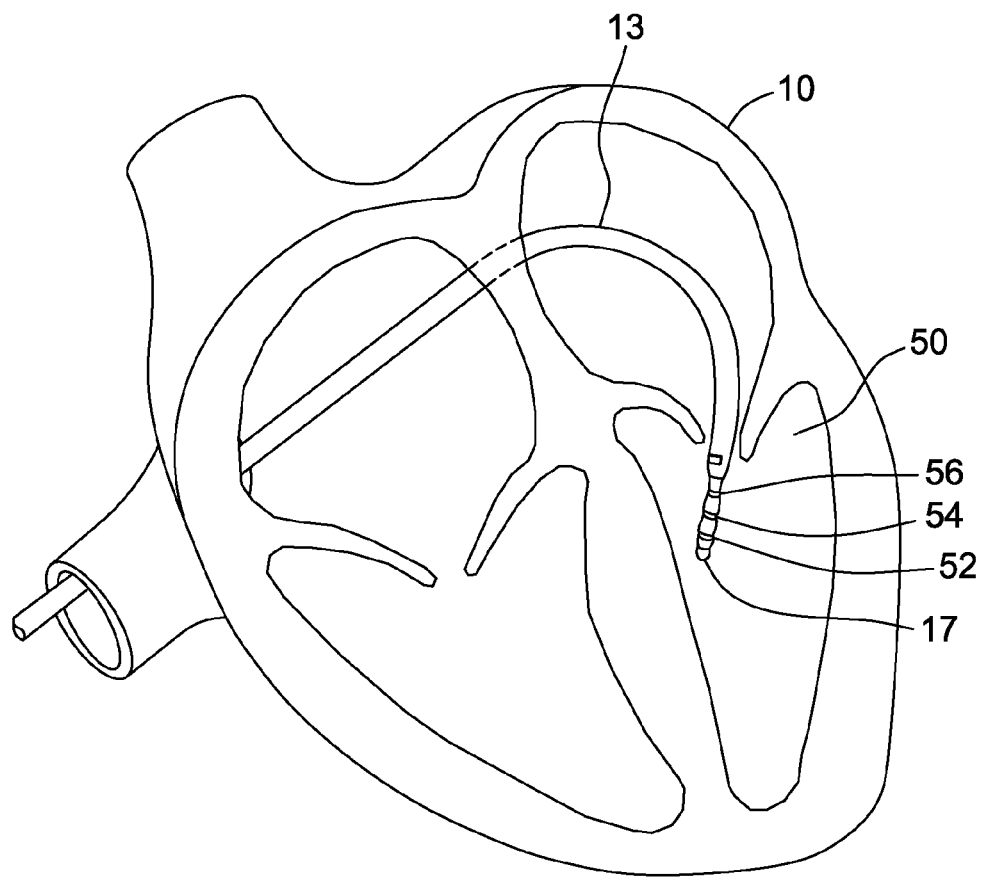
FIG. 2 is a schematic representation of a heart investigated by an electrophysiology catheter with several distal electrodes.
Figure 3:
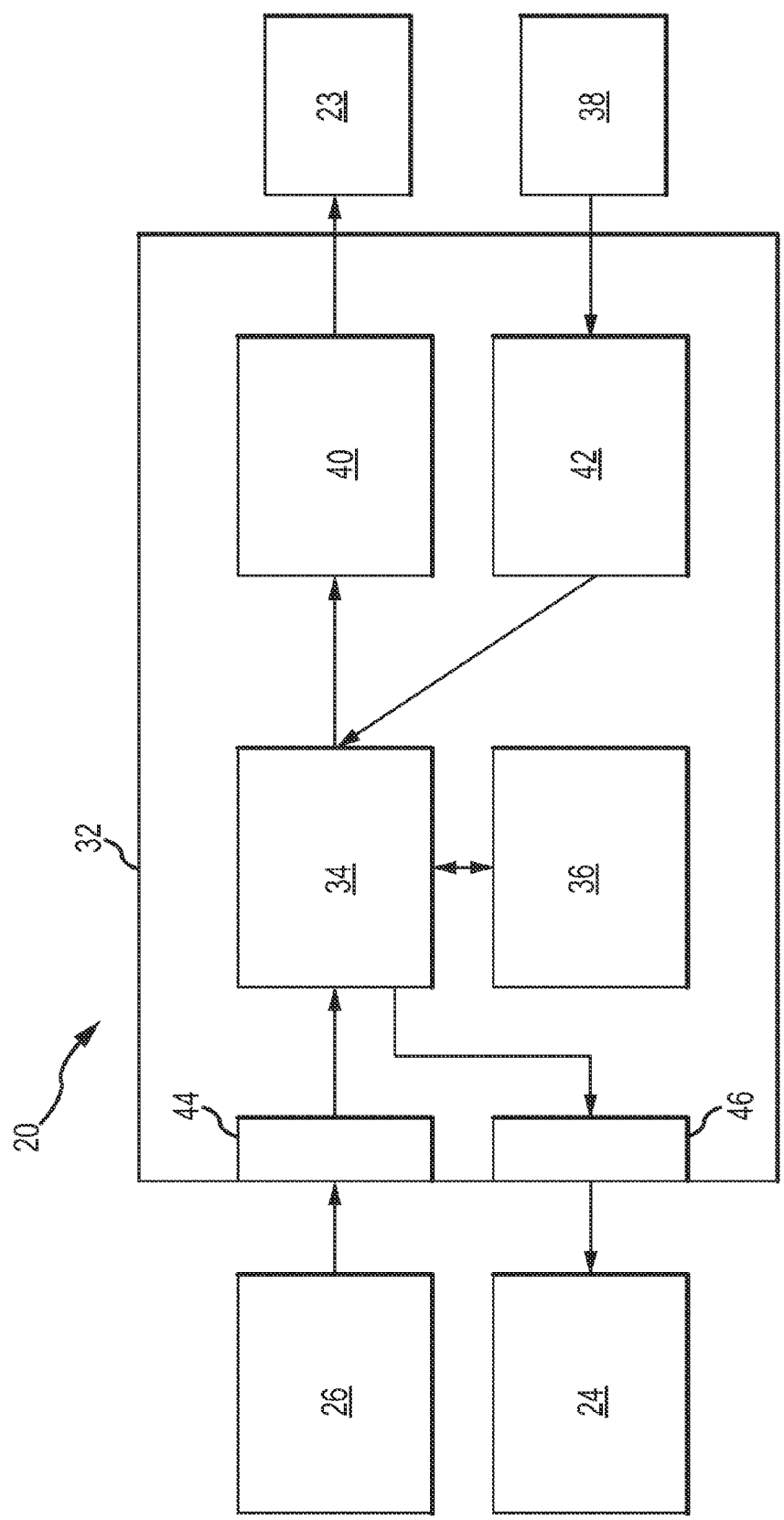
FIG. 3 is a schematic block diagram of a computing device for use in the system shown in FIG. 1.

With reference now to the drawings and in particular to FIGS. 1-3, one example of a system 8 is illustrated for conducting cardiac electrophysiology studies by navigating a cardiac catheter into a heart 10 of a patient 11 to measure electrical activity occurring in the heart and to three-dimensionally map the electrical activity and/or information related to or representative of the electrical activity. The system 8 is particularly used to measure electrophysiology data at a plurality of points along an endocardial surface, and store the measured data in association with location information for each measurement point at which the electrophysiology data was measured. In one embodiment, for example, the system 8 can instantaneously locate up to sixty-four electrodes in and/or around a heart and the vasculature of a patient, measure electrical activity at up to sixty-two of those sixty-four electrodes, and provide a three-dimensional map of time domain and/or frequency domain information from the measured electrical activity (e.g., electrograms) for a single beat of the heart 10. The number of electrodes capable of being simultaneously monitored is limited only by the number of electrode lead inputs into the system 8 and the processing speed of the system 8. The electrodes may be stationary or may be moving. In addition, the electrodes may be in direct contact with the wall of the heart, or may be merely generally adjacent to the wall of the heart, to collect the electrical activity. In another embodiment, an array of electrodes is used for collecting electrical activity at multiple locations along the wall of the heart. Such an array electrode is described in detail in U.S. Pat. No. 5,662,108, which is hereby incorporated by reference herein in its entirety.

In one suitable embodiment, the localization/mapping system 8 may be the EnSite™ Velocity™ navigation and visualization system available from St. Jude Medical, Inc. In other embodiments, any other suitable localization/mapping system may be used.

The patient 11 is depicted schematically as an oval for simplicity. Three sets of surface electrodes (e.g., patch electrodes) are shown applied to a surface of the patient 11 along an X-axis, a Y-axis, and a Z-axis. The X-axis surface electrodes 12, 14 are applied to the patient along a first axis, such as on the lateral sides of the thorax region of the patient (e.g., applied to the patient's skin underneath each arm) and may be referred to as the Left and Right electrodes. The Y-axis electrodes 18, 19 are applied to the patient along a second axis generally orthogonal to the X-axis, such as along the inner thigh and neck regions of the patient, and may be referred to as the Left Leg and Neck electrodes. The Z-axis electrodes 16, 22 are applied along a third axis generally orthogonal to the X-axis and the Y-axis, such as along the sternum and spine of the patient in the thorax region and may be referred to as the Chest and Back electrodes. The heart 10 lies between these pairs of surface electrodes. An additional surface reference electrode (e.g., a "belly patch") 21 provides a reference and/or ground electrode for the system 8. The belly patch electrode 21 is an alternative to a fixed intra-cardiac electrode 31. It should also be appreciated that in addition, the patient 11 will have most or all of the conventional electrocardiogram (ECG) system leads in place. This ECG information is available to the system 8 although not illustrated in the FIG. 1.

A representative catheter 13 having at least a single electrode 17 (e.g., a distal electrode) is also shown. This representative catheter electrode 17 is referred to as the "roving electrode" or "measurement electrode" throughout the specification. Typically, multiple electrodes on the catheter will be used. In one embodiment, for example, the system 8 may comprise up to sixty-four electrodes on up to twelve catheters disposed within the heart and/or vasculature of the patient. Of course, this embodiment is merely exemplary, and any number of electrodes and catheters may be used within the scope of the present invention.

The fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrode 17. The fixed reference electrode 31 may be used in addition to or alternatively to, the surface reference electrode 21 described above. In many instances, a coronary sinus electrode or other fixed electrode in the heart 10 can be used as a reference for measuring voltages and displacements.

Each surface electrode is coupled to the multiplex switch 24, and the pairs of electrodes are selected by software running on a computer 20, which couples the electrodes to a signal generator 25. The computer 20, for example, may comprise a conventional general-purpose computer, a special-purpose computer, a distributed computer, or any other type of computer. The computer 20 may comprise one or more processors, such as a single central-processing unit, or a plurality of processing units, commonly referred to as a parallel processing environment. The signal generator 25 excites a pair of electrodes, for example the Y-axis electrodes 18, 19, which generates an electric field in the body of the patient 11 and the heart 10.

During the delivery of the current pulse, the remaining surface electrodes are referenced to the surface electrode 21, and the voltages induced on these remaining electrodes are filtered via a low pass filter (LPF) 27. The LPF 27 may, for example, comprise an anti-aliasing filter (e.g., a 300 Hz analog LPF). The output of the LPF 27 is then provided to an analog-to-digital (A/D) converter 26 that converts the analog signal to a digital data signal. Further low pass filtering of the digital data signal may be subsequently performed by software executed on the computer 20 to remove electronic noise and cardiac motion artifact. This filtering may, for example, comprise a user-selectable cutoff frequency used to reduce noise. In this manner, the user can customize the system to trade off signal noise against signal fidelity according to the user's individual preferences. In this fashion, the surface electrodes are divided into driven and non-driven electrode sets. A pair of surface electrodes (e.g., the X-axis electrodes 12, 14) are driven by the signal generator 25, and the remaining, non-driven surface electrodes and other reference electrodes, if any, (e.g., the Y-axis electrodes 18, 19, the Z-axis electrodes 16, 22, the surface reference electrode 21, and, if present, the fixed reference electrode 31) are used as references to synthesize the position of any intracardial electrodes.

Generally, three nominally orthogonal electric fields are generated by a series of driven and sensed electric dipoles in order to realize catheter navigation in a biological conductor. Alternately, these orthogonal fields can be decomposed and any pairs of surface electrodes can be driven as dipoles to provide effective electrode triangulation. Additionally, such nonorthogonal methodologies add to the flexibility of the system. For any desired axis, the potentials measured across an intra-cardiac electrode 17 resulting from a predetermined set of drive (source-sink) configurations are combined algebraically to yield the same effective potential as would be obtained by simply driving a uniform current along the orthogonal axes. Thus, any two of the surface electrodes 12, 14, 16, 18, 19, 22 may be selected as a dipole source and drain with respect to a ground reference, e.g., the belly patch 21, while the unexcited electrodes measure voltage with respect to the ground reference. The measurement electrode 17 placed in the heart 10 is exposed to the field from a current pulse and its voltage is measured with respect to ground, e.g., with respect to the belly patch 21. In practice, the catheters within the heart may contain multiple electrodes, and each electrode potential may be measured. As previously noted, at least one electrode may be fixed to the interior surface of the heart to form a fixed reference electrode 31, which is also measured with respect to ground. Data sets from each of the surface electrodes, the internal electrodes, and the virtual references are all used to determine the location of the measurement electrode 17 or other electrodes within the heart 10.

All of the raw electrode voltage data is measured by the A/D converter 26 and stored by the computer 20 under the direction of software. This electrode excitation process occurs rapidly and sequentially as alternate sets of surface electrodes are selected and the remaining non-driven electrodes are used to measure voltages. This collection of voltage measurements is referred to herein as the "electrode data set." The software has access to each individual voltage measurement made at each electrode during each excitation of each pair of surface electrodes. The raw electrode data is used to determine the "base" location in three-dimensional space (X, Y, Z) of the electrodes inside the heart, such as the roving electrode 17, and any number of other electrodes located in or around the heart and/or vasculature of the patient 11. FIG. 2 shows a catheter 13, which may be a conventional electrophysiology (EP) catheter, extending into the heart 10. In FIG. 2, the catheter 13 extends into the left ventricle 50 of the heart 10. The catheter 13 comprises the distal electrode 17 discussed above with respect to FIG. 1 and has additional electrodes 52, 54, and 56. Since each of these electrodes lies within the patient (e.g., in the left ventricle of the heart in this example), location data may be collected simultaneously for each of the electrodes. In addition, when the electrodes are disposed adjacent to the surface, although not necessarily directly on the surface of the heart, and when the signal source 25 is "off" (i.e., when none of the surface electrode pairs is energized), at least one of the electrodes 17, 52, 54, and 56 can be used to measure electrical activity (e.g., voltage) on the surface of the heart 10.

In summary, the system 8 first selects a set of electrodes and then drives them with current pulses. While the current pulses are being delivered, electrical activity, such as the voltages measured at least one of the remaining surface electrodes and in vivo electrodes are measured and stored. At this point, compensation for artifacts, such as respiration and/or impedance shifting may be performed as indicated above. As described above, various location data points are collected by the system 8 that are associated with multiple electrode locations (e.g., endocardial electrode locations). Each point in the set has coordinates in space. In one embodiment, the system 8 collects location data points for up to sixty-four electrodes that may be located on up to twelve catheters simultaneously or in close proximity to one another. However, smaller or larger data sets may be collected and result in less complex and lower resolution or more complex and higher resolution representations of the heart, respectively.

The electrode data may also be used to create a respiration compensation value used to improve the raw location data for the electrode locations as described in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

The data used to determine the location of the electrode(s) within the heart are measured while the surface electrode pairs impress an electric field on the heart. A number of electrode locations may be collected by either sampling a number (e.g., sixty-two electrodes spread among up to twelve catheters) simultaneously or in sequence (e.g., multiplexed) and/or by sampling one or more electrodes (e.g., the roving electrode 17) being moved within the patient (e.g., a chamber of the heart). In one embodiment, the location data for individual electrodes are sampled simultaneously, which allows for collection of data at a single stage or phase of a heartbeat. In another embodiment, location data may be collected either synchronously with one or more phases of the heartbeat or without regard for any particular stage of the heartbeat. Where the data is collected across the phases of the heartbeat, data corresponding to locations along the wall of the heart will vary with time. In one variation, the data corresponding to the outer or inner locations may be used to determine the position of the heart wall at the maximum and minimum volumes, respectively.

For example, by selecting the most exterior points it is possible to create a "shell" representing the shape of the heart at its greatest volume.

A three-dimensional model of a portion of the patient, e.g., a region of the patient's heart or surrounding vasculature, may be created from the location data points, e.g., during the same or a previous procedure, or a previously generated three-dimensional model, e.g., a segmented CT or MRI scan image, may be used. A segmented model indicates that a subregion of a three-dimensional image has been digitally separated from a larger three-dimensional image, e.g., an image of the right atrium separated from the rest of the heart. Exemplary segmentation applications include ANALYZE (Mayo, Minneapolis, Minn.), Verismo™ (St. Jude Medical, Inc., St. Paul, Minn.), and CardEP (General Electric Medical Systems, Milwaukee, Wis.). Where the three-dimensional model is created from the location data points collected by the system 8, for example, during a single procedure, the exterior-most location points in the data can be used to determine a shape corresponding to the volume of a region of the patient's heart.

In one variation, for example, a convex hull may be generated using standard algorithms such as the Qhull algorithm. The Qhull algorithm, for example, is described in Barber, C. B., Dobkin, D. P., and Huhdanpaa, H. T., "The Quickhull algorithm for convex hulls," ACM Trans. on Mathematical Software, 22(4):469-483, December 1996. Other algorithms used to compute a convex hull shape are known and may also be suitable for use in implementing the invention. This surface is then re-sampled over a more uniform grid and interpolated to give a reasonably smooth surface stored as a three-dimensional model for presentation to the physician during the same or a later procedure. Such a three-dimensional model, for example, provides an estimated boundary of the interior of the heart region from the set of points.

FIG. 3 is a block diagram of the computer system 20. The computer system 20 includes the computing device 32, the display device 23, and the input device 38. The computing device 32 includes a display adapter 40 communicatively coupling the computing device 32 to the display device 23. Display device 23 may include, without limitation, a monitor, a television display, a plasma display, a liquid crystal display (LCD), a display based on light emitting diodes (LED), a display based on a plurality of organic light-emitting diodes (OLEDs), a display based on polymer light-emitting diodes (PLEDs), a display based on a plurality of surface-conduction electron-emitters (SEDs), a display including a projected and/or reflected image or any other suitable electronic device or display mechanism. In one embodiment, display device 23 includes a touch-screen with an associated touch-screen controller. An interface adapter 42 couples the computing device 32 to the input device 38. Computing device 32 includes an input 44 configured to receive electrode signals through A/D converter 26. An output 46 couples control signals from computing device 32 to multiplex switch 24. Input device 38 includes, without limitation, a keyboard, a keypad, a touch-sensitive screen, a mouse, a scroll wheel, a pointing device, an audio input device employing speech-recognition software, and/or any suitable device that enables a user to input data into computing device 32. In some embodiments, input device 38 and display device 23 are integrated into a single input/display device, such as in a touch screen display device.

The computing device 32 includes a processor 34 and a memory device 36 coupled to the processor 34. The term "processor" refers herein generally to any programmable system including systems and microcontrollers, reduced instruction set circuits (RISC), application specific integrated circuits (ASIC), programmable logic circuits, field programmable gate array (FPGA), gate array logic (GAL), programmable array logic (PAL), digital signal processor (DSP), and any other circuit or processor capable of executing the functions described herein. The above examples are exemplary only, and thus are not intended to limit in any way the definition and/or meaning of the term "processor." Moreover, although a single processor is illustrated in FIG. 3, the processor 34 may include more than one processor and the actions described herein may be shared by more than one processor.

The memory device 36 stores program code and instructions, executable by the processor 34. When executed by the processor 34, the program code and instructions cause the processor 34 to operate as described herein. The memory device 36 may include, but is not limited to only include, non-volatile RAM (NVRAM), magnetic RAM (MRAM), ferroelectric RAM (FeRAM), read only memory (ROM), flash memory and/or Electrically Erasable Programmable Read Only Memory (EEPROM). Any other suitable magnetic, optical and/or semiconductor memory, by itself or in combination with other forms of memory, may be included in the memory device 36. The memory device 36 may also be, or include, a detachable or removable memory, including, but not limited to, a suitable cartridge, disk, CD ROM, DVD or USB memory. Although illustrated separate from the processor 34, memory device 36 may be integrated with the processor 34.

The memory device 36 stores instructions (e.g., software code) that, when executed by the processor 34, cause the processor 34 to operate as described above and in accordance with the methods set forth herein.

Various electrophysiology data may be measured and presented to a cardiologist through the display 23 of the system 8 shown in FIG. 1. The display 23, for example, may be used to show data to a user, such as a physician, and to present certain options that allow the user to tailor the configuration of the system 8 for a particular use. The display may include a three-dimensional model of the heart 10. The locations of electrodes on one or more catheters may be mapped to the three-dimensional model. Other data that may be mapped to the heart surface model include, for example, the magnitude of a measured voltage, the timing relationship of a signal with respect to heartbeat events. Further, the peak-to-peak voltage measured at a particular location on the heart wall may be mapped to show areas of diminished conductivity and may reflect an infarct region of the heart.

In one embodiment, atrial electrogram information, and in a more particular embodiment complex fractionated electrogram (CFE) information, may be mapped to the three-dimensional model. In one example, such mapping of CFE information may be useful to identifying and guiding ablation targets for atrial fibrillation. CFE information refers to irregular electrical activation (e.g., atrial fibrillation) in which an electrogram comprises at least two discrete deflections and/or perturbation of the baseline of the electrogram with continuous deflection of a prolonged activation complex (e.g., over a 10 second period). Electrograms having very fast and successive activations are, for example, consistent with myocardium having short refractory periods and micro-reentry.

The presence of CFE information can be detected from the electrophysiology (EP) information (e.g., electrograms) collected by an electrode. For example, time instant and/or other quantifications of the fractionation of the electrogram may be used to determine the presence and/or absence of CFE information. CFE information may be quantified using one or more indices.

In an example embodiment, a voltage-based index is used to characterize the fractionation of a given electrogram. The voltage-based index is a voltage-based isoelectric index (v-IEI). The value of v-IEI for a particular electrogram is an indication of how much of the electrogram consists of isoelectric portions. Less fractionated electrograms are typically associated with a greater percentage of isoelectric portions than more fractionated electrograms.

Figure 4:
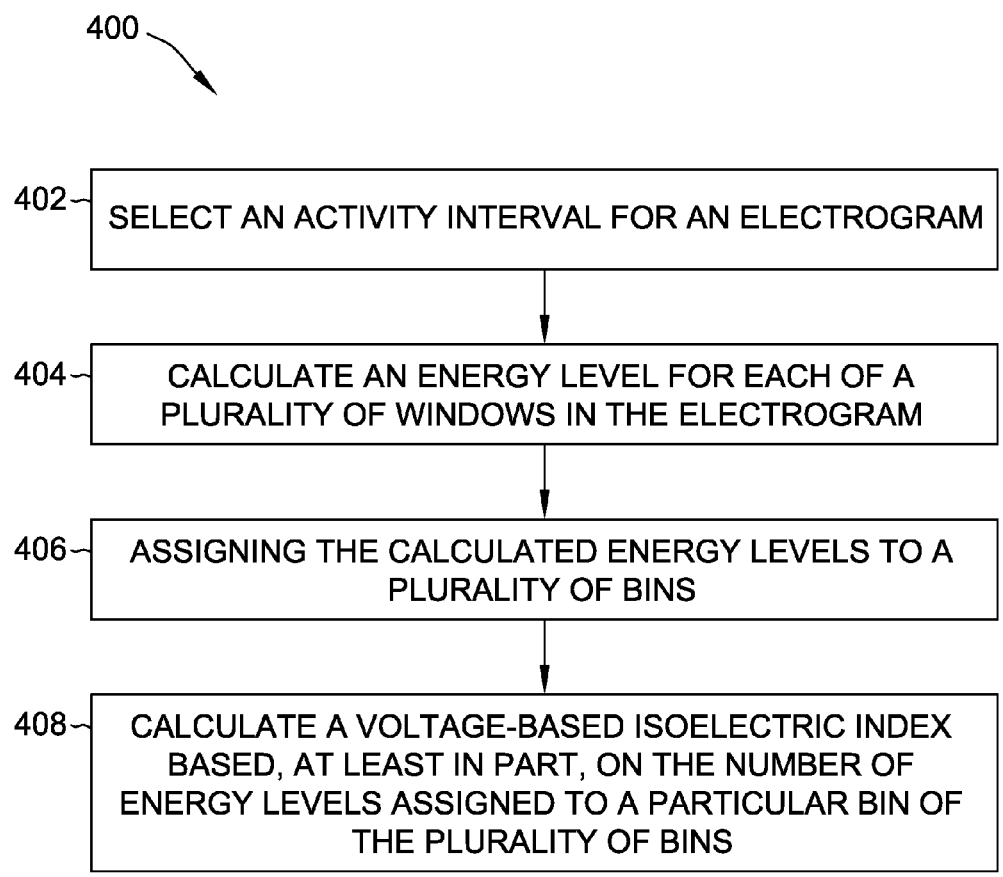
FIG. 4 is a flow diagram of an exemplary method for evaluating an electrogram segment.
Figure 5:
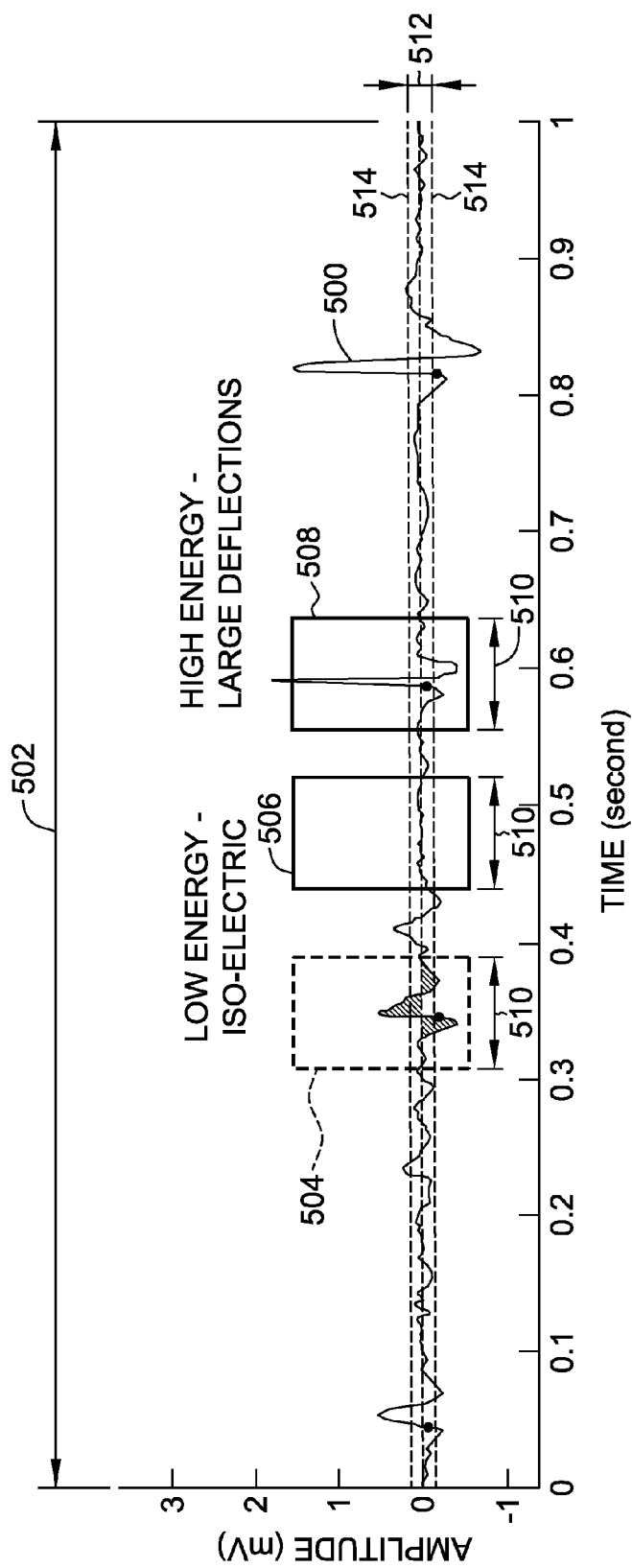
FIG. 5 is an example electrogram segment length for evaluation using the method shown in FIG. 4.

FIG. 4 is a flow diagram of an exemplary method 400 for evaluating an electrogram segment. The method 400 will be described with reference to the system 8 and the computing device 20, but may be implemented using any suitable electrophysiology devices and/or computing devices. FIG. 5 is an example electrogram 500 having a segment length 502. The electrogram 500 is graphed as an amplitude, in millivolts (mV) as a function of time, in seconds. In the illustrated example, the segment length 502 is about one second. The segment length 502 is variable and selectable by the user of the system 8, and the segment length 502 may be any suitable length of time. In some embodiments, the segment length is between five seconds and eight seconds.

At 402 of the method illustrated in FIG. 4, an activity interval is selected. The activity interval is a period of time that is shorter than the segment length. The activity interval defines a temporal window in which cardiac activity is searched for, and is generally selected to be long enough to capture typical cardiac activity, but small enough to include only temporally local phenomena. The activity interval may be user selected and/or a default activity interval may be predefined in computing device 20. In an example embodiment, the activity interval is selected to be 10 milliseconds (ms) by default. In other embodiments, any other suitable activity interval may be defined as a default activity interval. It should be understood that selecting the activity interval may include selecting a default activity interval by not specifying, changing, or selecting a different activity interval.

An energy level is calculated at 404 for a plurality of windows in the electrogram. Each window has a length equal to the activity interval. In an example embodiment, one window is defined for each sample (e.g., each discrete electrode measurement recorded by the system 8) in the electrogram, with the window beginning at the time of the sample and continuing for the length of the activity interval. Alternatively, the windows may begin at any other suitable time. Moreover, in some embodiments, more or fewer windows are defined. In one example embodiment, the sampling rate of the system 8 is about 2,034 samples per second. In other embodiments, the sampling rate of the system 8 is any other sampling rate that provides satisfactory resolution of the electrogram. In FIG. 5, three windows 504, 506 and 508 are shown, each of which is defined by an activity interval 510. For explanatory purposes, the windows 504, 506, and 508 are defined by an activity interval 510 of about 90 ms. In other embodiments, the activity interval may be selected to be a shorter length of time, such as about 10 ms. As described above, in an example embodiment, one window is defined for each sample in the electrogram segment. If the system 8 is sampling 2,034 samples per second, the one second long electrogram 500 shown in FIG. 5 would have 2,034 samples and up to 2,034 windows. For clarity and simplicity, only three windows 504, 506, and 508 of the 2,034 possible windows are shown in FIG. 5.

For each window in the electrogram, the energy level (also referred to sometimes as an activity level) is calculated by summing the absolute value of the measured amplitude of each sample in the window. The calculation may be represented by:

$$E(i) = \Sigma_{n=n_0}^{n_0+N-1} |V(n)| \quad (1)$$

where $E(i)$ is the energy level of the $i^{th}$ window, N is the number of samples in the window, $n_0$ is the first sample in the window, and $V(n)$ is the voltage of the $n^{th}$ sample. In an example embodiment, the sampling rate of the system 8 is about 2,034 samples per second, the activity interval is about 10 ms, and each window includes about twenty samples. After the energy level has been calculated for each window of the segment, the system 8 will have M separate energy values, where M is the number of windows defined for the electrogram segment. As can be seen in FIG. 5, window 506, which includes a generally isoelectric portion of the electrogram segment with an amplitude around zero, will have a much lower energy level $E(i)$ than windows 504 and 508, which include multiple small deflections and a large deflection respectively.

With reference back to FIG. 4, the calculated energy levels are assigned to a plurality of bins at 406. The bins define a histogram with a range from the minimum calculated energy level $E(i)$ to the maximum calculated energy level $E(i)$. The bins are each assigned a non-overlapping range of possible energy values between the minimum $E(i)$ and the maximum $E(i)$, such that every possible energy value between the minimum and the maximum values of $E(i)$ are associated with a bin. The size of the range of each bin is determined by the number of bins, with the range of calculated $E(i)$ values divided equally among the bins. In other embodiments, the bins need not all have a same range size. In an example embodiment, the number of bins is a fixed, predetermined number of bins. In another embodiment, the number of bins is a user selectable number of bins. In other embodiments, the number of bins is determined by the system 8, as will be described in more detail below.

Figure 6:
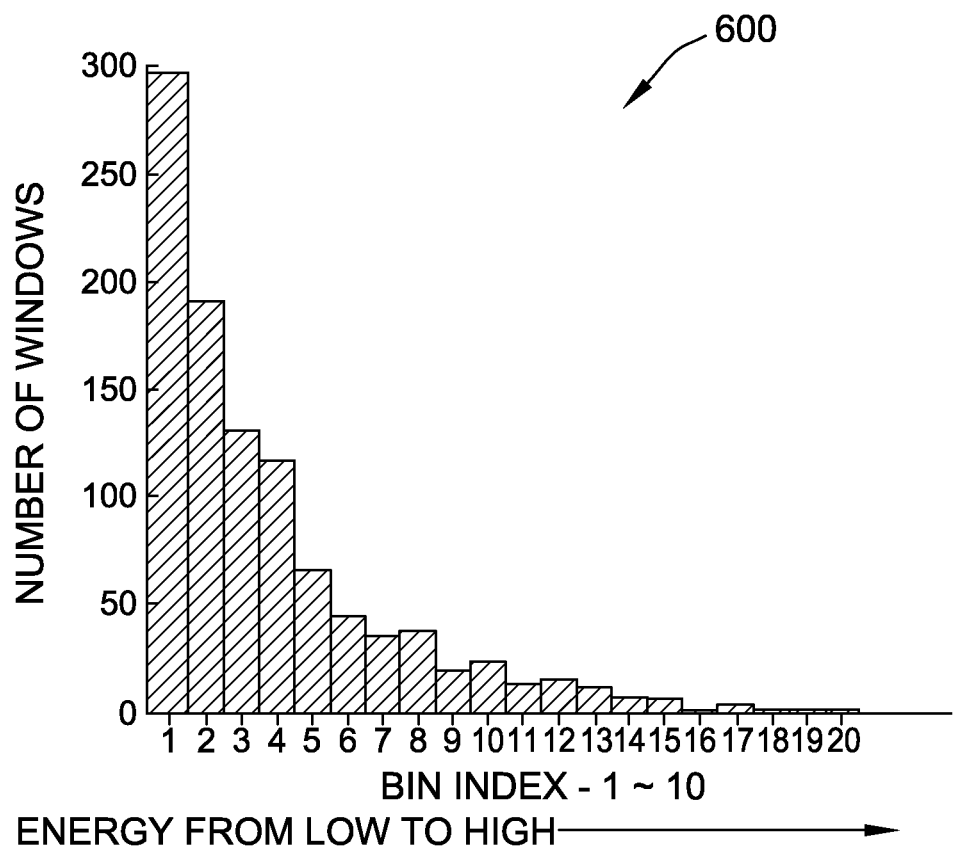
FIG. 6 is an example histogram produced using the method shown in FIG. 4.

The energy value $E(i)$ for each window is assigned to the bin with the energy range that encompasses the energy value $E(i)$ of that window. The system 8 tracks the number of windows assigned to each bin. This data is used to populate a histogram of the number of windows in each bin ordered from lowest energy bin to highest energy bin. An example histogram 600 with twenty bins is shown in FIG. 6. When organized from lowest energy values to highest energy values as shown in FIG. 6, the first bin is the bin that includes the window(s) having the lowest energy values, including the windows with an energy value $E(i)$ equal to the minimum energy value $E(i)$. As mentioned above, low energy value windows are typically associated with isoelectric portions of the electrogram. Thus, the lowest energy first bin $B_n(1)$ is associated with isoelectric portions of the electrogram segment.

Referring again to FIG. 4, at 408 a voltage-based isoelectric index (v-IEI) is calculated based at least in part on the number of energy values $E(i)$ assigned to a particular bin of the plurality of bins. In the exemplary embodiment, the particular bin is the bin with the lowest energy values. When organized by increasing energy value, the particular bin is the first bin. The v-IEI is calculated as:

$$v - IEI = \frac{B_n(1)}{M} \quad (2)$$

where $B_n(1)$ is the number of energy values E(i) assigned to the first (lowest energy) bin and M is the total number of energy values E(i) calculated for the electrogram segment (i.e., the number of windows defined for the electrogram segment). The index v-IEI is the ratio of low energy windows to all windows in the electrogram segment. The index v-IEI may be expressed as a percentage by multiplying the result of equation (2) by 100%. A low percentage v-IEI describes an electrogram segment with a small percentage of (or no) isoelectric portions, which may indicate a high level of fractionation. Conversely, a high percentage v-IEI describes an electrogram segment with a high percentage of isoelectric portions, which may indicate a low level of (or no) fractionation. The calculated v-IEI may be used on its own as an index describing the amount of fractionation in an electrogram segment. The v-IEI may be displayed numerically, mapped to a three dimensional map of the heart, or presented to a user of the system 8 in any suitable manner. Additionally, or alternatively, the v-IEI may be combined with one or more other indices to create a composite, or fused, index of fractionation.

Figure 7:
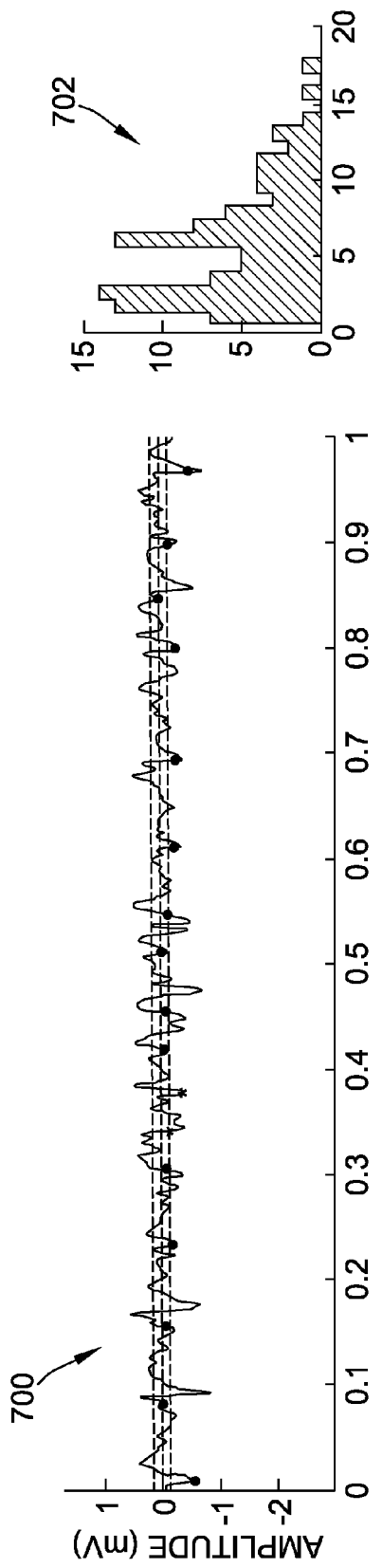
FIG. 7 is an example electrogram with a relatively high degree of fractionation and a histogram for the electrogram.
Figure 8:
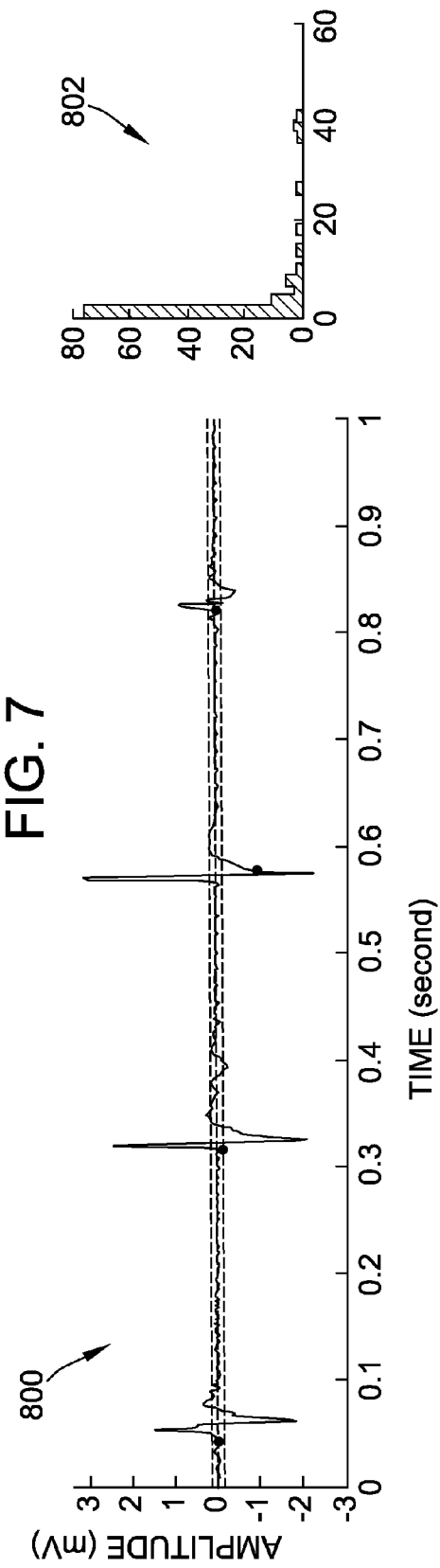
FIG. 8 is an example electrogram with a relatively low degree of fractionation and a histogram for the electrogram.

FIGS. 7 and 8 are example electrogram segments and associated histograms produced according to the method described herein. FIG. 7 includes an electrogram 700 with a one second segment length and a relatively high degree of fractionation. A 10 ms activity interval was selected, and the energy level E(i) was calculated for each window on the electrogram 700. The calculated energy levels were assigned to about twenty bins, as shown in the histogram 702. The v-IEI calculated for the electrogram 700 was 0.0693 (or 6.93%). FIG. 8 includes an electrogram 800 with a one second segment length and very little fractionation. A 10 ms activity interval was selected, and the energy level E(i) was calculated for each window on the electrogram 800. The calculated energy levels were assigned to about sixty bins (some bins contain no energy levels), as shown in the histogram 802. The v-IEI calculated for the electrogram 800 was 0.8624 (or 86.24%).

Figure 9:
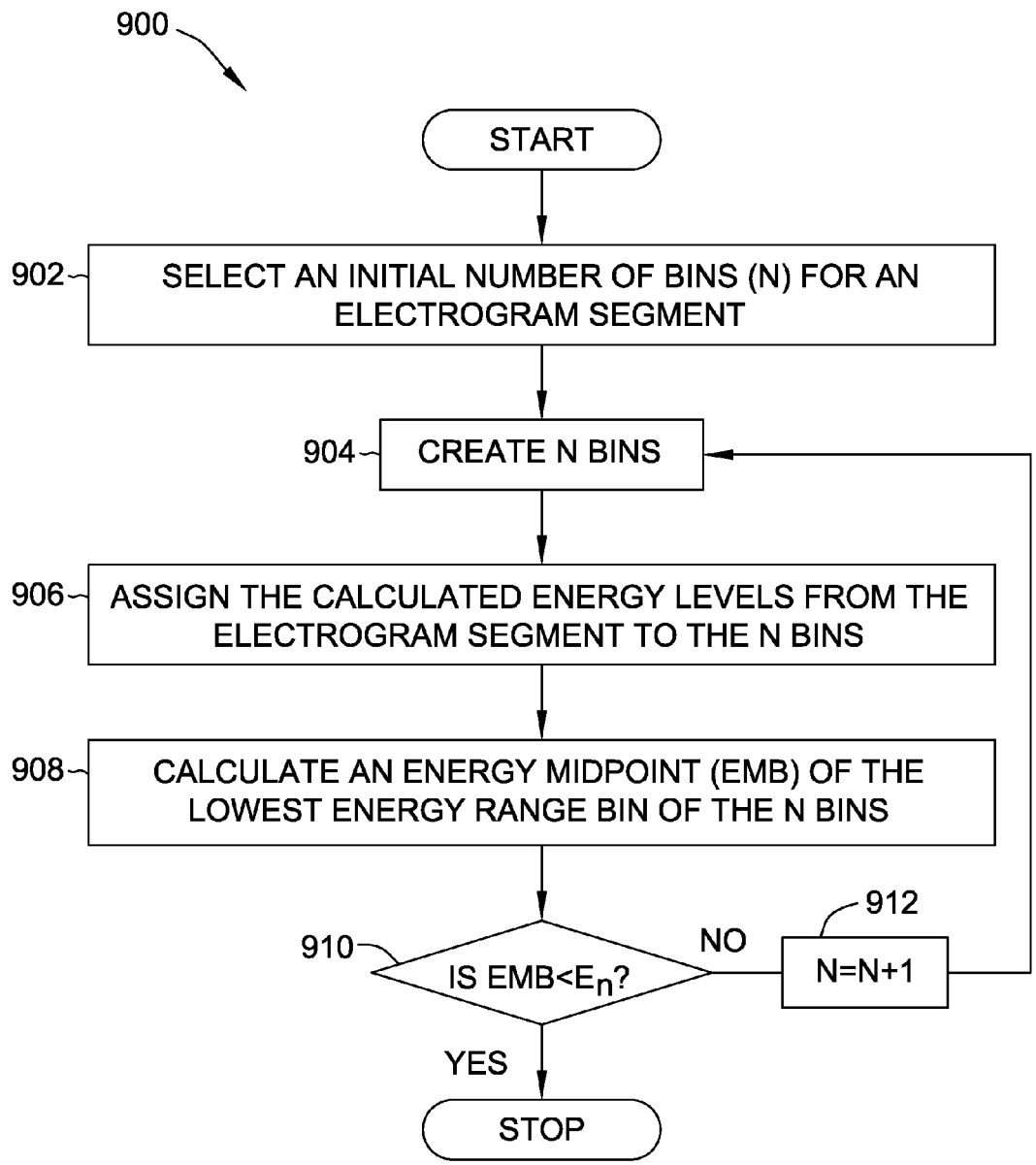
FIG. 9 is a flow diagram of an exemplary method for determining the number of bins for use in a method of calculating a voltage-based isoelectric index.

As mentioned above, in some embodiments the number of bins to which the energy levels E(i) are assigned is determined by the system 8 (and more particularly, by the computing device 20). The number of bins is found using an adaptive binning method to determine a number of bins that produces a lowest energy bin that accurately collects windows including isoelectric intervals. FIG. 9 is a flow diagram of an exemplary method 900 for determining the number of bins for use in a method of calculating a voltage-based isoelectric index, such as in the method 400 shown in FIG. 4. The method 900 is applied to data collected for a particular electrogram.

At 902, an initial number of bins (N) is selected for the electrogram segment. Because the method 900 is an adaptive iterative algorithm, the closer that the initial number of bins is set to the final number of bins, the fewer iterations will be needed to reach the final number of bins. Reducing the number of iterations may reduce the amount of processing needed to be performed and free computational power for other uses. Setting the initial N too high, however, may prevent the method 900 from determining a proper number of bins to achieve the desired correlation between the lowest energy bin and windows containing isoelectric segments. Accordingly, in some embodiments, the initial number of bins is selected to be one bin. In other embodiments, the initial N is selected to be ten bins. In other embodiments, the initial N is selected to be any number greater than one and less than an anticipated final number of bins. The initial number of bins may be user selected and/or a default value may be predefined in computing device 20. In an example embodiment, a default value for the initial number of bins is set as ten bins. In other embodiments, any other suitable default value for the initial N may be selected. It should be understood that selecting the initial number of bins may include selecting/accepting a default initial N by not specifying, changing, or selecting a number N.

At 904, N number of bins are created. Each bin has a range of energy values as described above. At 906, the energy values calculated for each window defined for the electrogram segment are assigned to the bin having a range in which its energy value is contained.

The energy midpoint (EMB) of the lowest energy bin is calculated at 908. The energy midpoint is calculated by:

$$EMB = E_{min} + \frac{E_{max} - E_{min}}{2N} \quad (3)$$

where $E_{min}$ is the lowest energy value for the electrogram segment, $E_{max}$ is the highest energy value for the electrogram segment, and N is the number of bins.

At 910, the energy midpoint EMB is compared to a noise level energy threshold $E_n$, which will be described in more detail below. If the EMB is less than the noise level energy threshold $E_n$, the method 900 is completed and the number of bins is set at the current number of bins N. If the EMB is not less than the $E_n$, the method 900 continues to 912. At 912, the number of bins N is incremented by one and the method 900 returns to 904. Thus, the method 900 continues with the number of bins increasing in each iteration until the EMB is less than the $E_n$.

In an exemplary embodiment, the energy noise level threshold $E_n$ is determined based on a peak-to-peak sensitivity setting of the system 8. The sensitivity setting is typically a user selected value. Alternatively, or additionally, the sensitivity setting may be a default/preset sensitivity setting. The peak-to-peak sensitivity setting is an voltage amplitude (A) in millivolts. In FIG. 5, for example, the peak-to-peak sensitivity 512 is defined by thresholds 514. To determine the threshold $E_n$, an energy level is calculated for a hypothetical sinusoidal noise signal between one half A and negative one half A. The frequency of the sinusoidal signal is determined by the frequency of the alternating current (AC) power supplied to the system 8. If the system 8 uses 60 Hz AC power, the hypothetical sinusoidal noise signal has a frequency of 60 Hz. When the system 8 is powered by 50 Hz AC power, a 50 Hz hypothetical sinusoidal noise signal is used. The energy level is calculated for one window of the selected activity interval according to equation (1). In other embodiments, any other suitable energy noise level threshold $E_n$, including a predetermined $E_n$ and/or a differently calculated $E_n$, may be used.

As discussed above, the voltage-based isoelectric index v-IEI may be utilized as an index by itself or may be combined with one or more other indices. A study of the v-IEI index and CFE mean for a large sample (around 50,000) of electrogram segments using scatter plots and correlation demonstrated no linear correlation between v-IEI and CFE mean. The v-IEI and CFE mean appear to be relating complimentary information. In one example embodiment, the v-IEI metric is combined with the CFE mean to provide a hybrid index for evaluation of electrogram segments. Alternatively, the v-IEI index may be combined with any other index for evaluation of electrograms including, for example, CFE StdDev, SCI, ACI, and ICL.

To combine the v-IEI and the CFE mean, the two indices need to have the same range of values. The v-IEI index ranges between zero and one, while the CFE mean ranges from zero to the length of the electrogram segment in milliseconds. In some embodiments, the maximum segment length, and accordingly the maximum CFE mean, is 8,000 ms. To map the CFE mean onto a range from zero to one, a sigmoid function is used. The sigmoid function for the conversion is:

$$f(x) = \frac{1}{1 + e^{(\beta(x-T))}} \quad (4)$$

where x is the original CFE mean, β is 0.035, and T is 125 ms. The parameter T in equation (4) may be treated as a center of interest. Variations around the center of interest will be more pronounced than variations farther away from the center of interest. The value of T=125 ms corresponds to a suggested CFE mean cutoff point between CFAE electrograms and non CFAE electrograms. Alternatively, T may have a different value to highlight a different range of CFE mean values. The parameter β governs the slope of the sigmoid function. The larger the value of β, the sharper the slope of the sigmoid function will be. Thus, β may be selected based on the range of data in which one is interested. In other embodiments, a different sigmoid function, a linear function, and/or another suitable monotonic function may be used to map the CFE mean and v-IEI to the same range.

After the CFE mean values are mapped to the same range as the v-IEI using equation (4), the v-IEI and CFE mean values may be combined. In one example, the v-IEI and CFE mean are combined using an F-measure. With two metrics $M_1$ and $M_2$, the F-measure (also referred to as an F1 score) is:

$$F_1 = 2\frac{M_1 M_2}{M_1 + M_2} \quad (5)$$

The F-measure produced by combining v-IEI and CFE mean values using equation (5) assigns equal weight to the v-IEI and CFE mean values. In some embodiments, the v-IEI values are given more weight in the combination by using a more general form of the F-measure:

$$F_\alpha = (1 + \alpha^2)\frac{M_1 M_2}{\alpha^2 * M_1 + M_2} \quad (6)$$

where α is a weighting factor, $M_1$ is the CFE mean, and $M_2$ is the v-IEI. The variable α gives different weighting to the harmonics of equation (6). The value of α is positive. If the value of α is 1, equation (6) reduces to equation (5) and $M_1$ and $M_2$ receive equal emphasis. If the value of α is smaller than 1, $M_1$ receives more emphasis than $M_2$. If the value of α is greater than 1, more emphasis is placed on $M_2$ than $M_1$. In an example embodiment, equation (6) was used to combine v-IEI and CFE mean values using α=1.0954. This value of α resulted from analysis of experimental results from application of the techniques described herein to an existing dataset of electrograms. Thus, slightly more weight was applied to the v-IEI values in the combination. In other embodiments any other suitable value may be used for α.

Figure 10:
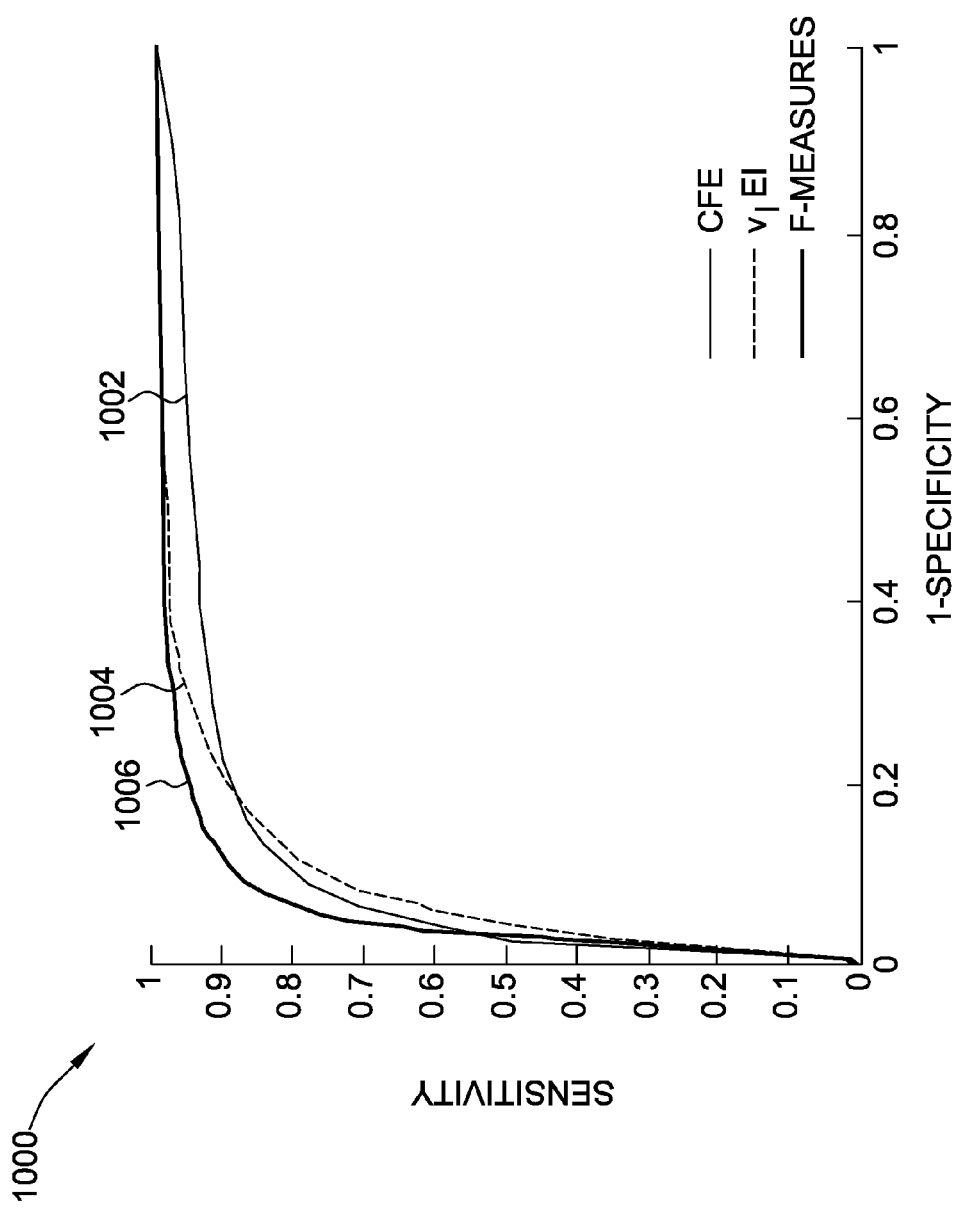
FIG. 10 is a graph of the results of a receiver operating characteristic (ROC) analysis.

The methods described herein were applied to several sample electrograms to determine the v-IEI. The determined the v-IEI and CFE mean were combined using equations (4) and (6), with α=1.0954 in equation (6). The v-IEI, CFE mean, and combined metric were evaluated for agreement with the expert annotations of the sample electrograms. A receiver operating characteristic (ROC) analysis was used to compare the v-IEI, CFE mean, and combined metric. FIG. 10 is a graph 1000 summarizing the results. In the graph, trace 1002 is the CFE mean, trace 1004 is the v-IEI, and 1006 is the F-measure combined CFE mean and v-IEI. The graph 100 generally shows greater sensitivity and specificity achieved using the F-measure than is achieved using the CFE mean alone.

For v-IEI mapping, in one embodiment, two parameters may be set: a refractory parameter and a floor parameter. The refractory parameter defines a minimum segment length considered to be iso-electric. For example, the refractory parameter may be in a range from 30 milliseconds (ms) to 60 ms. The floor parameter determines a maximum peak to peak voltage to be considered iso-electric. For example, the floor parameter may be in a range from 0.03 millivolts (mV) to 0.05 mV, or above a noise floor. In one embodiment, when a user adjusts at least one of the refractory parameter and the floor parameter, an v-IEI map is recomputed and redisplayed. An overall segment length (e.g., segment length 502 (shown in FIG. 5)) is also specified. The overall segment length may be, for example, in a range from 1 second(s) to 8 s.

The relationship between v-IEI and CFE has been experimentally demonstrated. For example, for an overall segment length of one second, the following Table 1 lists experimental data obtained for a plurality of electrograms:

TABLE 1

|  | CFE < 120 ms | v-IEI < 25% | v-IEI < 20% |
| --- | --- | --- | --- |
| % of all Electrograms | 24.70 ± 11.28% | 9.16 ± 6.75% | 6.9 ± 5.3% |
| % of Electrograms with CFE < 120 ms | 100% | 98.42 ± 1.40% | 98.64 ± 1.46% |
| % of Electrograms with v-IEI < 25% | 32.58 ± 14.07% | 100% | 100% |

In Table 1, the first row of the table (i.e., "% of all Electrograms") represents the percentage of all acquired electrograms that fit the criterion of the respective columns. For example, 24.70% of all acquired electrograms had a CFE mean of less than 120 ms. The second and third rows represent the additional criterion for the column electrograms. For example, 98.42% of the electrograms that had a v-IEI index under 25% were also electrograms with a CFE mean of less than 120 ms. Further, 32.58% of electrograms with a CFE mean of less than 120 ms, had a v-IEI index under 25%. Accordingly, from the experimental data of Table 1, it is apparent that the CFE mean and v-IEI index are related to one another. Other, similar experiments were also conducted with similar results.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements. The use of terms indicating a particular orientation (e.g., "top", "bottom", "side", etc.) is for convenience of description and does not require any particular orientation of the item described.

As various changes could be made in the above without departing from the scope of the disclosure, it is intended that all matter contained in the above description and shown in the accompanying drawings shall be interpreted as illustrative and not in a limiting sense.

What is claimed is:

1. A computer implemented method for evaluating an electrogram containing a plurality of data samples each having a voltage, the computer implemented method comprising:
   selecting an activity interval for the electrogram;
   defining a plurality of windows, each window of the plurality of windows being a length of time defined by the activity interval;
   calculating an energy level for each window of the plurality of windows of the electrogram based on the voltages of the data samples in each window;
   defining a plurality of bins;
   assigning the calculated energy levels to the plurality of bins defining a histogram with a range from a minimum calculated energy level to a maximum calculated energy level, such that every possible energy level between the minimum and the maximum values are associated with a bin;
   calculating an index based at least in part on a number of energy levels assigned to a particular bin of the plurality of bins; and
   presenting the index to a user on a display to indicate fractionation of the electrogram.

2. The computer implemented method of claim 1, wherein defining the plurality of windows comprises defining one window for each sample of data in the electrogram.

3. The computer implemented method of claim 1, wherein calculating an energy level for each window comprises summing an absolute value of the voltage of each data sample in the window.

4. The computer implemented method of claim 1, wherein each bin of the plurality of bins is associated with a range of energy levels, and wherein assigning the calculated energy levels to the plurality of bins comprises assigning each energy level to the bin associated with the range of energy levels that contains said energy level.

5. The computer implemented method of claim 1, wherein defining the plurality of bins comprises determining how many bins to define by iteratively increasing the number of bins until a midpoint of the bin with the lowest energy range of energy levels is less than a noise threshold value.

6. The computer implemented method of claim 5, further comprising defining the noise threshold value as a function of a sensitivity setting for the electrogram.

7. The computer implemented method of claim 1, wherein each bin of the plurality of bins is associated with a range of energy levels, and wherein calculating an index based at least in part on a number of energy levels assigned to a particular bin comprises calculating an index based at least in part on a number of energy levels assigned to the bin with the lowest energy range of energy levels.

8. The computer implemented method of claim 1, further comprising generating a histogram of the number of energy levels assigned to each bin of the plurality of bins.

9. The computer implemented method of claim 1, further comprising combining the calculated index with a second index for the electrogram to produce a fused index.

10. The computer implemented method of claim 9, wherein the second index is a complex fractionated electrogram (CFE) mean, and combining the calculated index with the CFE mean comprises mapping the CFE mean to a same range of values as the calculated index using a sigmoid function and combining the calculated index with the mapped CFE mean using an F-measure function.

11. The computer implemented method of claim 1 further comprising displaying the index numerically to a user.

12. The computer implemented method of claim 1 further comprising mapping the index to a three-dimensional map of a heart presented on the display.

13. A system for evaluating an electrogram containing a plurality of data samples each having a voltage, the system comprising:
   a computing device configured to receive the data samples, the computing device comprising:
     a processor; a display coupled to said processor;
     at least one memory device coupled to said processor, the memory device storing computer-executable instructions that, when executed by the processor, cause the computing device to:
       define a plurality of windows, each window of the plurality of windows being a length of time defined by an activity interval;
       calculate an energy level for each window of the plurality of windows of the electrogram based on the voltages of the data samples in each window;
       define a plurality of bins;
       assign the calculated energy levels to the plurality of bins defining a histogram with a range from a minimum calculated energy level to a maximum calculated energy level, such that every possible energy level between the minimum and the maximum values are associated with a bin;
       calculate an index based at least in part on a number of energy levels assigned to a particular bin of the plurality of bins; and
       present the index to a user on the display to indicate fractionation of the electrogram.

14. The system of claim 13, wherein the memory device further stores computer-executable instructions that, when executed by the processor, cause the computing device to define one window for each sample of data in the electrogram.

15. The system of claim 13, wherein the memory device further stores computer-executable instructions that, when executed by the processor, cause the computing device to calculate the energy level for each window by summing an absolute value of the voltage of each data sample in the window.

16. The system of claim 13, wherein each bin of the plurality of bins is associated with a range of energy levels, and wherein the memory device further stores computer-executable instructions that, when executed by the processor, cause the computing device to assign each energy level to the bin associated with the range of energy levels that contains said energy level.

17. The system of claim 13, wherein the memory device further stores computer-executable instructions that, when executed by the processor, cause the computing device to determine how many bins to define by iteratively increasing the number of bins until a midpoint of the bin with the lowest energy range of energy levels is less than a noise threshold value.

18. The system of claim 17, wherein the memory device further stores computer-executable instructions that, when executed by the processor, cause the computing device to define the noise threshold value as a function of a sensitivity setting for the electrogram.

19. The system of claim 13, wherein each bin of the plurality of bins is associated with a range of energy levels, and wherein the particular bin of the plurality of bins is the bin with the lowest energy range of energy levels.

20. The system of claim 13, further comprising a display device, wherein the memory device further stores computer-executable instructions that, when executed by the processor, cause the computing device to generate a histogram of the number of energy levels assigned to each bin of the plurality of bins.

21. The system of claim 13, wherein the memory device further stores computer-executable instructions that, when executed by the processor, cause the computing device to combine the calculated index with a second index for the electrogram to produce a fused index.

22. The system of claim 21, wherein the second index is a complex fractionated electrogram (CFE) mean, and wherein the memory device further stores computer-executable instructions that, when executed by the processor, cause the computing device to map the CFE mean to a same range of values as the calculated index using a sigmoid function and combine the calculated index with the mapped CFE mean using an F-measure function.

23. The system of claim 13, wherein the memory device further stores computer-executable instructions that, when executed by the processor, cause the computing device to display the index numerically to a user.

24. The system of claim 13, wherein the memory device further stores computer-executable instructions that, when executed by the processor, cause the computing device to map the index on a three dimensional map of a heart presented on the display.

25. A computer implemented method for evaluating an electrogram containing a plurality of data samples each having a voltage, the computer implemented method comprising:
selecting an activity interval for the electrogram;
defining a plurality of windows, each window of the plurality of windows being a length of time defined by the activity interval;
calculating respective energy levels for each window of the plurality of windows of the electrogram based on a summation of absolute values of the voltages of each data sample in each window;
defining a first bin and a second bin;
assigning the respective energy levels and corresponding windows to one of the first bin and the second bin;
calculating an index based on a ratio of the respective energy levels in the first bin to a total number of the plurality of windows; and
presenting the index to a user on a display to indicate fractionation of the electrogram.

26. The computer implemented method of claim 25, wherein defining the plurality of windows comprises defining one window for each sample of data in the electrogram.

27. The computer implemented method of claim 25, wherein the first bin is associated with a low energy level range and the second bin is associated with a high energy level range, and wherein assigning the respective energy levels to one of the first bin and the second bin comprises assigning the respective energy levels to the bin associated with the range of energy levels that contains the respective energy level.

28. The computer implemented method of claim 25, further comprising generating a histogram of the number of energy levels assigned to the first bin and the second bin.

29. The computer implemented method of claim 25, further comprising combining the calculated index with a second index for the electrogram to produce a fused index.

30. The computer implemented method of claim 29, wherein the second index is a complex fractionated electrogram (CFE) mean, and combining the calculated index with the CFE mean comprises mapping the CFE mean to a same range of values as the calculated index using a sigmoid function and combining the calculated index with the mapped CFE mean using an F-measure function.

31. The computer implemented method of claim 25 further comprising displaying the index numerically to a user.

32. The computer implemented method of claim 25 further comprising mapping the index to a three-dimensional map of a heart presented on the display.

* * * * *